United States Patent [19]

Tieman

[11] 4,153,626

[45] May 8, 1979

[54] PREPARATION OF α-CYANOBENZYL ESTERS

[75] Inventor: Charles H. Tieman, Modesto, Calif.

[73] Assignee: Shell Oil Company, Houston, Tex.

[21] Appl. No.: 860,507

[22] Filed: Dec. 14, 1977

[51] Int. Cl.$^2$ .......................................... C07C 121/66
[52] U.S. Cl. .............................................. 260/465 D
[58] Field of Search .................................. 260/465 D

[56] References Cited

U.S. PATENT DOCUMENTS

| 3,835,176 | 9/1974 | Matsuo et al. ................... 260/465 D |
| 3,996,244 | 12/1976 | Fuyimoto et al. ............ 260/332.2 A |

*Primary Examiner*—Dolph H. Torrence

[57] ABSTRACT

α-Cyanobenzyl esters are prepared by treating an acid halide with a benzaldehyde cyanohydrin in the presence of a Lewis acid catalyst.

18 Claims, No Drawings

PREPARATION OF α-CYANOBENZYL ESTERS

The present invention is directed to a new process for the preparation of α-cyanobenzyl esters.

SUMMARY OF THE INVENTION

The present invention is directed to a process for the preparation of α-cyanobenzyl esters which comprises treating a carboxylic acid halide with a benzaldehyde cyanohydrin in the presence of a Lewis acid catalyst. Preferably, such a reaction is conducted in the presence of an inert solvent under refluxing conditions.

The α-cyanobenzyl esters, which are prepared by the present process and which include those that are part of the class often referred to as synthetic pyrethroids, have the formula I

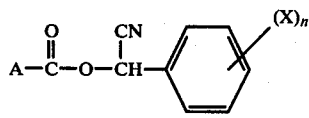

wherein A is an optionally-substituted aralkyl, alkyl or cycloalkyl group containing up to 24 carbon atoms, X is an alkyl, alkenyl, aralkyl or aryloxy group containing up to 10 carbon atoms, and n is an integer of from 1 to 3.

Preferably n is 1 and X is in the 3 position relative to the benzyl carbon atom. Generally speaking, X is an alkyl group containing 1 to 6 carbon atoms, especially methyl, an alkenyl group containing 2 to 4 carbon atoms, such as allyl, or an aralkyl or aryloxy groups preferably contain up to 8 carbon atoms, such as benzyl or especially phenyloxy.

It should be noted that optical isomers, cis-trans isomers and other kinds of geometric isomers of the compounds according to formula I are within the scope of the present invention as well as racemates and mixtures of isomers of one or more of the pesticidally active compounds according to formula I. The various isomers of the compounds according to formula I may have different insecticidal toxicities and/or knock down potency.

When A represents an optionally-substituted cycloalkyl group in formula I, the preferred compounds are those containing a cyclopropyl group of formula II

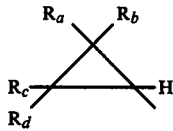

wherein $R_a$ and $R_b$ each represent an alkyl group having from 1 to 6 carbon atoms, especially methyl, a halogen atom having an atomic number of from 9 to 35, inclusive, especially a chlorine atom, or when $R_a$ represents a hydrogen atom then $R_b$ represents an alkenyl group having from 2 to 6 carbon atoms optionally substituted by from 1 to 3 fluorine, chlorine and/or bromine atoms, especially an isobutenyl, a mono- or dichlorovinyl or dibromovinyl group; $R_c$ and $R_d$ each represent an alkyl group having 1 to 6 carbon atoms, or when $R_c$ is hydrogen then $R_d$ is an alkenyl group having 2 to 6 carbon atoms optionally substituted by from 1 to 3 fluorine, chlorine and/or bromine atoms, or at least one of $R_a$ and $R_b$ together or $R_c$ and $R_d$ together each represent an alkylene group having from 2 to 6, especially 3, carbon atoms.

When A represents an optionally-substituted aralkyl group in formula I, preferred compounds are those containing a substituted benzyl group of formula II

wherein $R^3$ is an alkyl, cycloalkyl or alkenyl group containing up to 4 carbon atoms and $R^1$ is a hydrogen atom, a halogen atom having an atomic number of from 9 to 53, inclusive, $NO_2$, $CF_3$, an alkyl group containing from 1 to 4 carbon atoms, an alkoxy group containing from 1 to 2 carbon atoms, an allyl group or a propargyl group, and $R^2$ is a hydrogen atom or a methyl group.

Preferred because of their pesticidal properties are those pyrethroids wherein A is a benzyl group of formula III in which $R^3$ is a branched chain alkyl group such as isopropyl, $R^1$ is a halogen atom or an alkyl or alkoxy group, for example, a chlorine atom, methyl or methoxy and $R^2$ is a hydrogen atom.

Suitably the acid halide reactants are those in which the halogen atom attached to the carbonyl carbon atom has an atomic number of from 17 to 53, preferably chlorides or bromides.

The pyrethroid compounds are known in art as pesticides as for example when A is a cyclopropyl group of formula II: U.S. Pat. Nos. 3,835,176, 3,987,193, Netherlands publication Nos. 7,307,130, 7,212,973, 7,205,298, Belgian patents Nos. 814,819, 820,418, German publication No. 2,407,024 or are disclosed in pending U.S. patent application Ser. No. 771,236, now U.S. Pat. No. 4,100,298, or when A is an optionally substituted benzyl group of formula III: Belgian patent No. 801,946; or when A is an alkyl group: Belgian patent No. 842,061.

The most preferred α-cyanobenzyl pyrethroids for use in pesticidal composition have the formula I wherein A is alpha-isopropyl-4-chlorobenzyl, 2,2,3,3-tetramethylcyclopropyl, 2-(2,2,-dichlorovinyl)-3,3-dimethylcyclopropyl, or 2-(2,2-dibromovinyl)-3,3-dimethylcyclopropyl, X is 3-phenoxy and n is 1.

The catalyst may be any Lewis acid: that is a compound which will accept one or more pairs of electrons from another compound to form a coordinate covalent bond. Suitably, the Lewis acid is derived from an element of Group IIIA of the Periodic Table of Elements (Lange, Handbook of Chemistry 8th Edition, pages 56–57) titanium, tin, antimony, tantalum, rhenium, iron or zinc. These include inorganic compounds, derived from boron, aluminum, gallium, indium, thallium, zinc, titanium, antimony iron and the like. Generally, the inorganic Lewis acid halides and cyanides are preferred. These include boron trichloride, boron tribromide, aluminium chloride, aluminium bromide, gallium trichloride, gallium tribromide, titanium tetrachloride, titanium tetrabromide, stannic chloride, stannic bromide, antimony pentachloride, tantalum pentachloride, rhenium pentachloride, ferric chloride and especially zinc salts, such as zinc chloride, zinc iodide or zinc cyanide.

Optimum amounts of Lewis acid depend on the particular catalyst chosen, the solvent and the reaction components as well as the reaction time and product purity desired. Usually the molar ratio of catalyst to cyanohydrin is from 1:5 to 1:500, preferably 1:10 to 1:100.

The solvent should be inert to the reaction. Suitable solvents include alkane, cycloalkane and aromatic hydrocarbons, chlorinated hydrocarbons or ethers and mixtures thereof. More particularly the solvent is an alkane containing 5 to 10 carbon atoms such as n-pentane, n-hexane, n-octane, n-heptane, n-nonane, n-decane and their isomers. Gasolines rich in alkanes are also very suitable, for example, with a boiling range at atomospheric pressure of between 40° and 65° C., 60° and 80° C. or 80° and 110° C. Petroleum ether is also suitable. Cyclohexane and methylcyclohexane are examples of cycloalkanes containing 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or a benzene ring, for example carbon tetrachloride, chloroform, dichloromethane, 1,2-dichloroethane, trichloroethane, perchloroethane, chlorobenzene and 1,2- and 1,3-dichlorobenzene. Ethers are generally those containing 2 to 6 carbon atoms such as diethyl ether and diisopropyl ether. Chlorinated hydrocarbons are preferred, especially methyl halides such as methylene chloride.

The molar ratio of the acid halide to benzaldehyde cyanohydrin is not critical and can be varied, e.g., from 1:3 to 3:1 and preferably from 1.5 to 1 to 1 to 1.5.

The preferred reaction temperature is such as to constitute refluxing conditions if at normal atmospheric pressure and will naturally vary as to the nature of the composition of the reaction mixture.

The various ingredients of the reaction mixture are contacted, preferably with agitation, e.g., stirring. The acid halide may also be gradually added to a mixture of the other starting compound and reaction ingredients.

Conventionally, after a Lewis acid catalyzed reaction has been completed, or has been carried out to a desired degree of conversion, it can be advantageous to inactivate the Lewis acid before any components of the reaction mixture are isolated. This inactivation of the Lewis acid can be conveniently accomplished by extraction of the reaction mixture with water.

The products of the process of the invention are then recovered by suitable techniques of filtration, distillation and the like.

In the case of the pyrethroids of formula I in which A is optionally-substituted benzyl, it is known that the ester of the (+)-S- acid and the (−)-S-cyanohydrin tend to be the most pesticidally active of the various isomers and are preferred for that reason. Such being the case, it is highly desirable to prepare more of the ester derived from the (+)-S-acid and (−)-S-cyanohydrin.

At least in the case of α-cyano-3-phenoxybenzyl α-isopropylphenylacetates, such as α-cyano-3-phenoxybenzyl α-isopropyl-p-chlorophenylacetate, the process of the present invention provides not only improved chemical purity of the product but a desired improvement in the amount of ester derived from the (+)-S-acid and the (−)-S-cyanohydrin. That is, the product ester contains unexpectedly more than 50% of the enantiomeric pair containing the (+)-S-acid (−)-S-cyanohydrin ester. Usually this is about 55%.

ILLUSTRATIVE EMBODIMENTS

The following embodiments are provided for the purpose of illustrating the invention and should not be regarded as limiting its scope in any way. The identity of the products was confirmed by GLC, infrared and nuclear magnetic resonance spectral analysis an necessary.

Embodiment I

A solution of 10.0 ml of 4-chloro-alpha-isopropylphenylacetyl chloride, 11.3 g of alpha-cyano-3-phenoxybenzenemethanol and 0.2 g of zinc chloride in 50 ml of methylene chloride was stirred and refluxed for three hours. The solution was cooled to room temperature and stirred with aqueous sodium bicarbonate for one hour. The organic phase was separated, dried with magnesium sulfate and evaporated at reduced pressure to afford 20.0 g (95% yield) of the desired product of 95% purity by GLC analysis.

Embodiment 2

A procedure similar to that of Embodiment 1, but using zinc iodide as a catalyst, gave 91% yield of the desired ester product of 92.4% purity by GLC analysis.

Embodiment 3

A reaction similar to Embodiment 1 using zinc cyanide as a catalyst gave 100% yield of the desired ester product of 80% purity by GLC analysis.

Following procedures similar to the Illustrative Embodiments set forth above, α-cyano-3-phenoxybenzyl 2,2-dimethyl-3-(2,2-dibromovinyl)cyclopropanecarboxylate, α-cyano-3-phenoxybenzyl 2,2-dimethyl-3-(2,2-dichlorovinyl)cyclopropanecarboxylate and α-cyano-3-phenoxybenzyl 2,2-dimethyl-3-isobutenylcyclopropanecarboxylate are obtained.

I claim:

1. A process for the preparation of an α-cyanobenzyl ester having the formula I

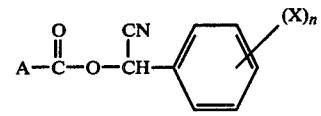

wherein A is
(a) a cyclopropyl group of formula II

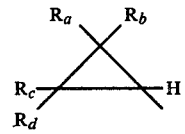

wherein $R_a$ and $R_b$ each is an alkyl group having from 1 to 6 carbon atoms, a halogen atom having an atomic number of from 9 to 35, inclusive or when $R_a$ is a hydrogen atom then $R_b$ is an alkenyl group having from 2 to 6 carbon atoms optionally substituted by from 1 to 3 fluorine, chlorine and/or bromine atoms; $R_c$ and $R_d$ each is an alkyl group having from 1 to 6 carbon atoms or when $R_c$ is a hydrogen atom then $R_d$ is an alkenyl group having 1 to 6 carbon atoms optionally substituted by from 1 to 3 fluorine, chlorine and/or bromine atoms, or at least one of $R_a$ and $R_b$ together or $R_c$ and $R_d$ together is an alkylene group having 2 to 6 carbon atoms or (b) an optionally substituted aralkyl group of the formula III

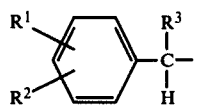

wherein $R^3$ is an alkyl, cycloalkyl or alkenyl group containing up to 4 carbon atoms and $R^1$ is a hydrogen atom, a halogen atom having an atomic number of from 9 to 53, inclusive, $NO_2$, $CF_3$, an alkyl group containing from 1 to 4 carbon atoms, and alkoxy group containing from 1 to 2 carbon atoms, an allyl group or a propargyl group and $R^2$ is a hydrogen atom or a methyl group; X is an alkyl, alkenyl, aralkyl or aryloxy group containing up to 10 carbon atoms; and n is an integar of from 1 to 3; which comprises contacting a carboxylic acid halide with a benzaldehyde cyanohydrin in the presence of a Lewis acid catalyst.

2. A process according to claim 1 wherein the reaction is conducted in the presence of an inert solvent under refluxing conditions.

3. A process according to claim 2 wherein the solvent is a hydrocarbon or chlorinated hydrocarbon.

4. A process according to claim 3 wherein the solvent is a chlorinated hydrocarbon containing from 1 to 3 chlorine atoms on a benzene ring or on an alkane chain containing from 1 to 4 carbon atoms.

5. A process according to claim 1 wherein the Lewis acid catalyst is an inorganic compound derived from an element of Group IIIA of the Periodic Table of Elements, titanium, tin, antimony, tantalum, rhenium, iron or zinc.

6. A process according to claim 5 wherein the Lewis acid catalyst is an inorganic halide.

7. A process according to claim 6 wherein the Lewis acid inorganic halide catalyst is a zinc halide.

8. A process according to claim 7 wherein the zinc halide is zinc chloride.

9. A process according to claim 5 conducted in the presence of an inorganic halide Lewis acid catalyst and a hydrocarbon or chlorinated hydrocarbon solvent under reflux conditions.

10. A process according to claim 5, wherein A is a benzyl group of formula III in which R is a branched chain alkyl group; $R^1$ is a halogen atom or an alkyl or alkoxy group and $R^2$ is a hydrogen atom.

11. A process according to claim 10, wherein A is α-isopropyl-p-chlorophenyl and X is 3-phenoxy.

12. A process according to claim 11 in which the Lewis acid catalyst is zinc chloride.

13. A process for the preparation of α-cyanobenzyl α-isopropyl phenylacetates having improved insecticidally active isomer content which comprises contacting an α-isopropyl phenylacetic acid halide with a benzaldehyde cyanohydrin in the presence of a Lewis acid catalyst in an inert solvent under refluxing conditions.

14. A process according to claim 13 wherein the solvent is a hydrocarbon or chlorinated hydrocarbon.

15. A process according to claim 13 wherein the Lewis acid catalyst is an inorganic compound derived from an element of Group IIIA of the Periodic Table of Elements, titanium, tin, antimony, tantalum, rhenium, iron or zinc.

16. A process according to claim 15 wherein the Lewis acid catalyst is an inorganic halide.

17. A process according to claim 16 wherein the α-isopropyl phenylacetic acid halide is an α-isopropyl p-chlorophenylacetic acid chloride or bromide and the benzaldehyde cyanohydrin is 3-phenoxybenzylcyanohydrin.

18. A process according to claim 17 wherein the Lewis acid catalyst is zinc chloride.